US012752049B2

(12) United States Patent
Younes et al.

(10) Patent No.: US 12,752,049 B2
(45) Date of Patent: Oct. 6, 2026

(54) RECTAL CATHETER ASSEMBLY

(71) Applicants: Kareem Younes, Santa Clarita, CA (US); Amelia Younes, Santa Clarita, CA (US)

(72) Inventors: Kareem Younes, Santa Clarita, CA (US); Amelia Younes, Santa Clarita, CA (US)

( * ) Notice: Subject to any disclaimer, the term of this patent is extended or adjusted under 35 U.S.C. 154(b) by 1012 days.

(21) Appl. No.: 17/949,027

(22) Filed: Sep. 20, 2022

(65) Prior Publication Data

US 2024/0091432 A1 Mar. 21, 2024

(51) Int. Cl.
*A61M 3/02* (2006.01)
*A61M 25/00* (2006.01)

(52) U.S. Cl.
CPC ......... *A61M 3/0295* (2013.01); *A61M 25/007* (2013.01)

(58) Field of Classification Search
CPC .. A61M 3/0295; A61M 25/007; A61M 31/00; A61M 2210/1067; A61M 3/0262
See application file for complete search history.

(56) References Cited

U.S. PATENT DOCUMENTS 8,905,981 B2 12/2014 Budig
D815,737 S 4/2018 Bergstrom
10,238,842 B2 3/2019 Gobel
10,765,796 B2 9/2020 Foley
D908,865 S 1/2021 Greenberg
11,027,055 B2 6/2021 Andreen
2019/0231969 A1 8/2019 Hougaard
2019/0358390 A1* 11/2019 Göbel .................. A61M 31/00
2021/0113761 A1 4/2021 Hvid

FOREIGN PATENT DOCUMENTS

CN 209933136 U * 1/2020
WO WO-2009153973 A1 * 12/2009 ........ A61M 37/0092
WO WO2018188710 10/2018

* cited by examiner

*Primary Examiner* — Bhisma Mehta
*Assistant Examiner* — Fatimata Sahra Diop

(57) ABSTRACT

A rectal catheter assembly includes a rectal catheter that has a plurality of fluid outlets and a balloon positioned around the rectal catheter. The balloon is inflatable thereby facilitating the balloon to seal a patient's rectum to inhibit fluids from leaking outwardly from the patient's rectum. A feed tube is fluidly coupled to the rectal catheter and the feed tube has a first injection port and a second injection port. The first injection port inflates the balloon and the second injection port delivers a medication into the rectal catheter. An extension tube is fluidly coupled to the feed tube and a bag is fluidly attached to the extension tube such that the bag is in fluid communication with the rectal catheter thereby facilitating the bag to deliver and subsequently receive a fluid enema solution to the rectal catheter.

8 Claims, 4 Drawing Sheets

RECTAL CATHETER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to catheter devices and more particularly pertains to a new catheter device for delivering and subsequently draining a rectal enema. The device includes a rectal catheter and a balloon positioned around the rectal catheter which is inflatable to seal a patient's rectum. The device includes a first injection port which inflates the balloon and a second injection port for delivering medication into the rectal catheter. A bag containing a fluid enema solution is fluidly coupled to the rectal catheter for delivering and subsequently recovering the fluid enema solution.

(2) Description of Related Art Including Information Disclosed Under 37 CFR 1.97 and 1.98

The prior art relates to catheter devices including an anal irrigation pump for inflating a balloon and a reservoir bag. The prior art discloses a catheter injection port device that includes a plurality of injection ports that can inflate multiple catheter balloons and inject a fluid medication. The prior art discloses a rectal catheter that is structured to buckle or fold axially and radially and which has a dumbbell shaped balloon. The prior art discloses a rectal catheter device that includes a valve for adjusting the flow of a fluid from an irrigation bag to a rectal catheter. The prior art discloses a rectal irrigation device that includes a rectal catheter, a balloon, a first pump for inflating the balloon and a second pump for delivering a fluid enema solution. The prior art discloses a rectal catheter that has a funnel shape. The prior art discloses an irrigation device that includes a stomal catheter.

BRIEF SUMMARY OF THE INVENTION

An embodiment of the disclosure meets the needs presented above by generally comprising a rectal catheter that has a plurality of fluid outlets and a balloon positioned around the rectal catheter. The balloon is inflatable thereby facilitating the balloon to seal a patient's rectum to inhibit fluids from leaking outwardly from the patient's rectum. A feed tube is fluidly coupled to the rectal catheter and the feed tube has a first injection port and a second injection port. The first injection port inflates the balloon and the second injection port delivers a medication into the rectal catheter. An extension tube is fluidly coupled to the feed tube and a bag is fluidly attached to the extension tube such that the bag is in fluid communication with the rectal catheter thereby facilitating the bag to deliver and subsequently receive a fluid enema solution to the rectal catheter.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
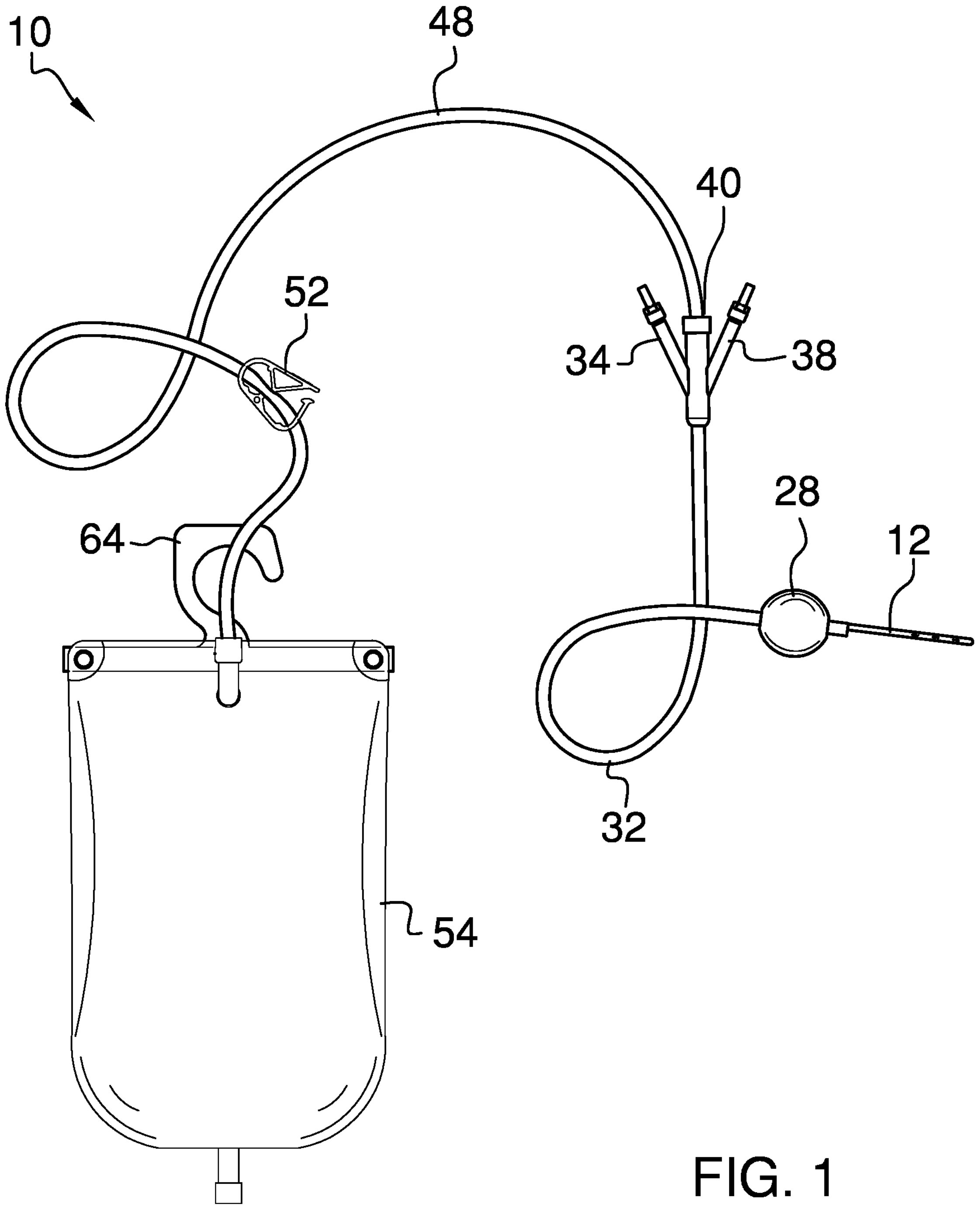
FIG. 1 is a perspective view of a rectal catheter assembly according to an embodiment of the disclosure.
Figure 2:
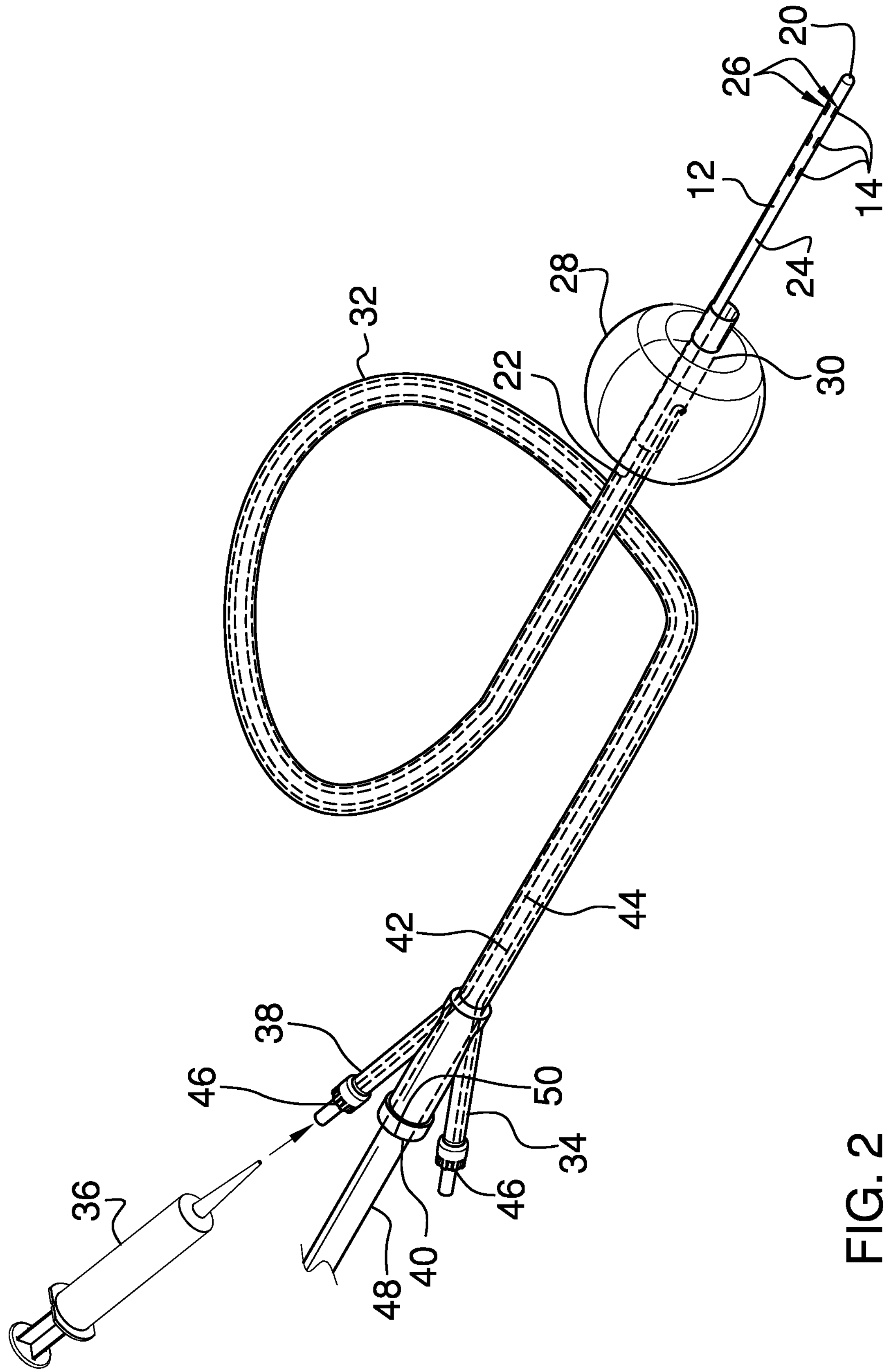
FIG. 2 is a phantom perspective view of a catheter and a feed tube of an embodiment of the disclosure.
Figure 3:
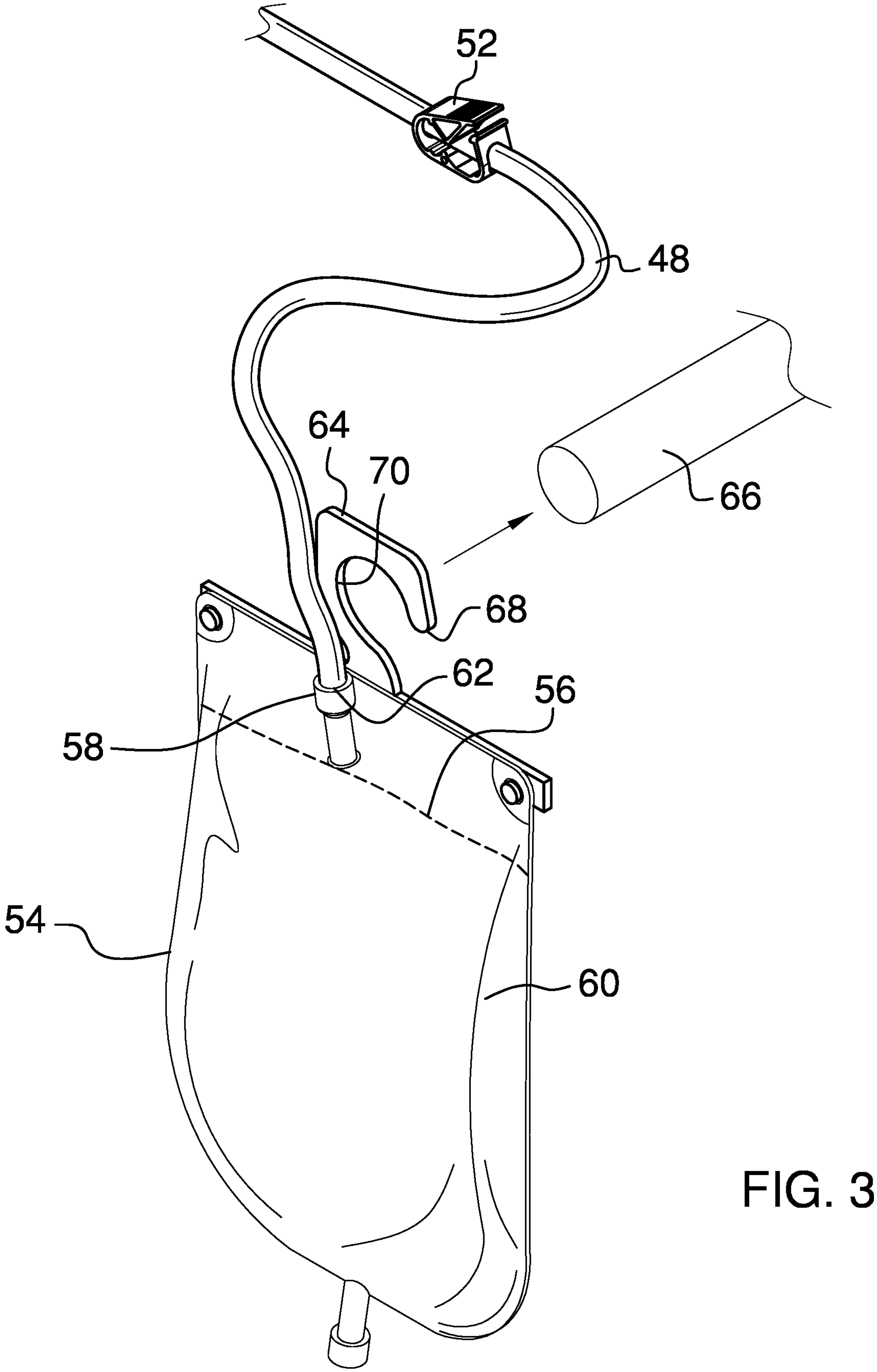
FIG. 3 is a perspective view of an extension tube and a bag of an embodiment of the disclosure.
Figure 4:
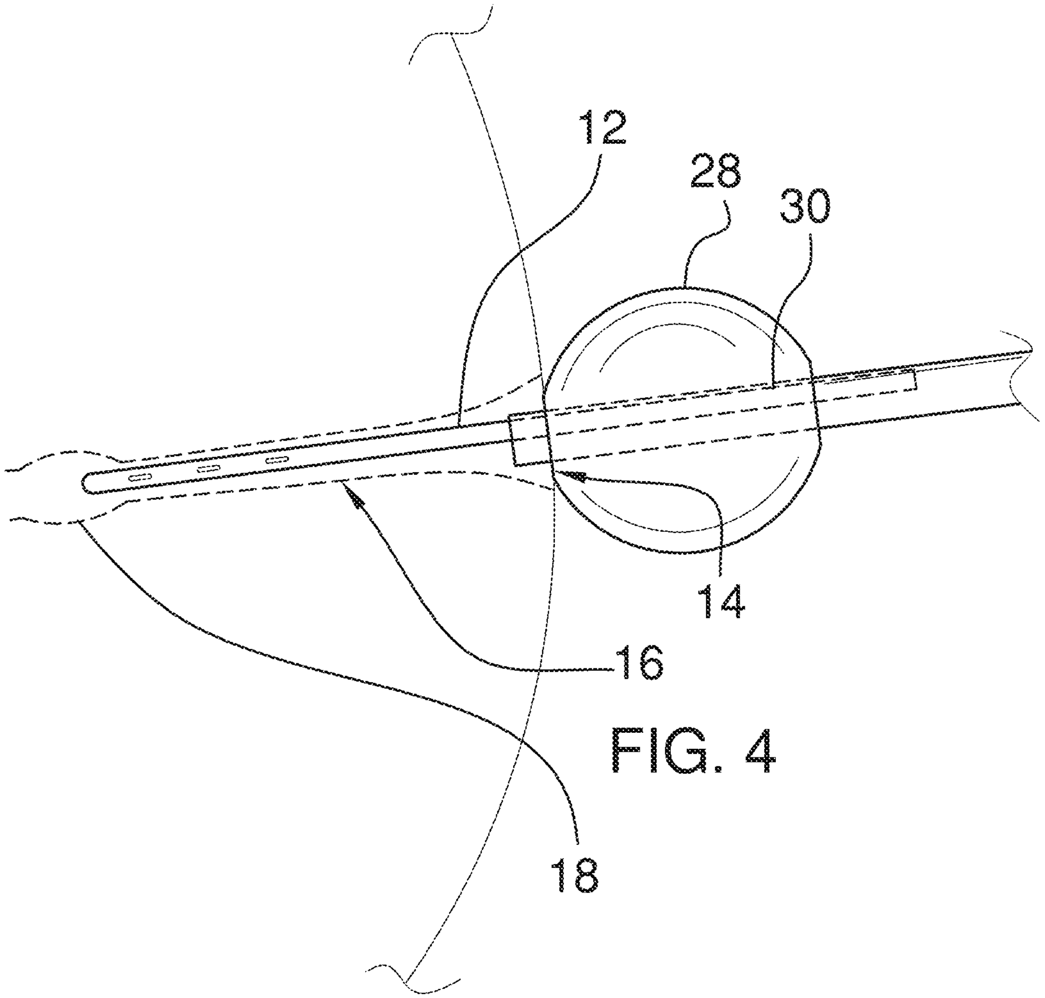
FIG. 4 is a perspective in-use view of an embodiment of the disclosure.

With reference now to the drawings, and in particular to FIGS. 1 through 4 thereof, a new catheter device embodying the principles and concepts of an embodiment of the disclosure and generally designated by the reference numeral 10 will be described.

As best illustrated in FIGS. 1 through 4, the rectal catheter assembly 10 generally comprises a rectal catheter 12 that has a plurality of fluid outlets 14. The rectal catheter 12 is insertable into a patient's rectum 16 such that the plurality of fluid outlets 14 is in fluid communication with the patient's colon 18. The rectal catheter 12 has a first end 20, a second end 22 and an outer wall 24 extending between the first end 20 and the second end 22 and each of the fluid outlets 14 extends through the outer wall 24. The plurality of fluid outlets 14 is arranged in plurality of rows 26 each extending from the first end 20 toward the second end 22. Each of the fluid outlets 14 is elongated along an axis extending between the first end 20 and the second end 22 such that each of the fluid outlets 14 has an ovoid shape. The rectal catheter 12 may have a length ranging between approximately 10.0 cm and 15.0 cm and diameter ranging between approximately 5.0 mm and 6.0 mm.

A balloon 28 is positioned around the rectal catheter 12 and the balloon 28 is inflatable thereby facilitating the balloon 28 to seal the patient's rectum 16 when the rectal catheter 12 is inserted into the patient's rectum 16. In this way the balloon 28 can inhibit fluids from leaking outwardly from the patient's rectum 16. The balloon 28 has a channel 30 extending through a center of the balloon 28 and the rectal catheter 12 extends through the channel 30 such that the balloon 28 is positioned adjacent to the second end 22 of the rectal catheter 12.

A feed tube 32 is provided and the feed tube 32 is fluidly coupled to the rectal catheter 12. The feed tube 32 has a first injection port 34 for insertably receiving an injection needle 36 and the feed tube 32 has a second injection port 38 for insertably receiving an injection needle 36. The first injection port 34 is in fluid communication with the balloon 28 for inflating the balloon 28 with the injection needle 36. The second injection port 38 is in fluid communication with the rectal catheter 12 for delivering a medication from the injection needle 36 into the rectal catheter 12. The feed tube 32 has a coupling port 40 that is in fluid communication with the rectal catheter 12. Each of the first injection port 34 and the second injection port 38 angle away from an outer wall 24 of the feed tube 32 at a point that is located adjacent to the coupling port 40.

The feed tube 32 has a first conduit 42 that is fluidly coupled between the first injection port 34 and the balloon 28 and the feed tube 32 has a second conduit 44 that is fluidly coupled between the second injection port 38 and the second end 22 of the rectal catheter 12. Each of the first injection port 34 and the second injection port 38 includes a fluid lock 46 that is positionable between a closed condition or an open condition to control a flow of fluid through the fluid lock 46. The fluid lock 46 associated with each of the first injection port 34 and the second injection port 38 may comprise a Luer-lock or other similar device.

An extension tube 48 is fluidly coupled to the feed tube 32 and the extension tube 48 has a primary end 50 that is insertable into the coupling port 40 on the feed tube 32. A tube lock 52 is attached to the extension tube 48 and the tube lock 52 compresses the extension tube 48 when the tube lock 52 is closed thereby inhibiting a fluid from flowing through the extension tube 48. Conversely, the tube lock 52 is released from compressing the extension tube 48 when the tube lock 52 is open thereby facilitating the fluid to flow through the extension tube 48. The tube lock 52 may comprise an intravenous pinch clamp or other similar device commonly employed for pinching intravenous tubes.

A bag 54 is fluidly attached to the extension tube 48 such that the bag 54 is in fluid communication with the rectal catheter 12. In this way the bag 54 can deliver and subsequently receive a fluid enema solution 56 to the rectal catheter 12. A fluid port 58 that is integrated into an outer wall 60 of the bag 54 and the fluid port 58 insertably receives a secondary end 62 of the extension tube 48. A hook 64 is coupled to and extends upwardly from the bag 54 thereby facilitating the bag 54 to be suspended from a support 66 to gravity feed the fluid enema solution 56 to the rectal catheter 12. The hook 64 has a distal end 68 and a front edge 70 extending between the bag 54 and the distal end 68. The front edge 70 is concavely arcuate between the bag 54 and the distal end 68 thereby facilitating the hook 64 to conform to a rod of an intravenous bag support rack.

In use, the rectal catheter 12 is inserted into the patient's rectum 16 and an injection needle 36, such as an intravenous syringe, is attached to the first injection port 34 to inflate the balloon 28. The extension tube 48 is attached to the bag 54 to facilitate the fluid enema solution 56 to be administered to the patient. Additional medications can be injected into the second injection port 38 to be administered with the fluid enema solution 56. The fluid enema solution 56 is subsequently captured by the bag 54 when the fluid enema solution 56 drains from the patient. In this way the fluid enema solution 56 can be administered and recovered without leakage or without the need to change fluid lines or accessories in the middle of the enema. The balloon 28 is deflated and the rectal catheter 12 is removed from the patient when the fluid enema solution 56 has been recovered into the bag 54.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A rectal catheter assembly for delivering and subsequently draining a rectal enema, said assembly comprising: a rectal catheter having a plurality of fluid outlets, said rectal catheter being insertable into a patient's rectum such that each of said plurality of fluid outlets is in fluid communication with the patient's colon; a balloon being positioned around said rectal catheter, said balloon being inflatable thereby facilitating said balloon to seal the patient's rectum wherein said balloon is configured to inhibit fluids from leaking outwardly from the patient's rectum; a feed tube being fluidly coupled to said rectal catheter, said feed tube having a first injection port for insertably receiving an injection needle, said feed tube having a second injection port for insertably receiving an injection needle, said first injection port being in fluid communication with said balloon for inflating said balloon with the injection needle, said second injection port being in fluid communication with said rectal catheter for delivering a medication from the injection needle into said rectal catheter, said feed tube having a coupling port being in fluid communication with said rectal catheter; an extension tube being fluidly coupled to said feed tube; and a bag being fluidly attached to said extension tube such that said bag is in fluid communication with said rectal catheter thereby facilitating said bag to deliver a fluid enema solution to said rectal catheter and subsequently receive the fluid enema back through said rectal catheter.

2. The assembly according to claim 1, wherein said rectal catheter has a first end, a second end and an outer wall extending between said first end and said second end, each of said plurality of fluid outlets extending through said outer wall, said plurality of fluid outlets being arranged in plurality of rows each extending from said first end toward said second end, each of said plurality of fluid outlets being elongated along an axis extending between said first end and said second end such that each of said plurality of fluid outlets has an ovoid shape.

3. The assembly according to claim 2, wherein said balloon has a channel extending through a center of said balloon, said rectal catheter extending through said channel such that said balloon is positioned adjacent to said second end of said rectal catheter.

4. The assembly according to claim 1, wherein:

each of said first injection port and said second injection port angles away from an outer wall of said feed tube at a point being located adjacent to said coupling port;

said feed tube has a first conduit being fluidly coupled between said first injection port and said balloon;

said feed tube has a second conduit being fluidly coupled between said second injection port and said second end of said rectal catheter; and each of said first injection port and said second injection port includes a fluid lock being positionable between a closed condition or an open condition to control a flow of fluid through said fluid lock.

5. The assembly according to claim 1, further comprising a tube lock being attached to said extension tube, said tube lock compressing said extension tube when said tube lock is closed thereby inhibiting a fluid from flowing through said extension tube, said tube lock being released from compressing said extension tube when said tube lock is open thereby facilitating the fluid to flow through said extension tube.

6. The assembly according to claim 1, wherein:

said extension tube has a primary end being insertable into said coupling port on said feed tube; and said bag has a fluid port being integrated into an outer wall of said bag, said fluid port insertably receiving a secondary end of said extension tube.

7. The assembly according to claim 1, further comprising a hook being coupled to and extending upwardly from said bag thereby facilitating said bag to be suspended from a support to gravity feed the fluid enema solution to said rectal catheter, said hook having a distal end and a front edge extending between said bag and said distal end, said front edge being concavely arcuate between said bag and said distal end thereby facilitating said hook to conform to a rod of an intravenous bag support rack.

8. A rectal catheter assembly for delivering and subsequently draining a rectal enema, said assembly comprising: a rectal catheter having a plurality of fluid outlets, said rectal catheter being insertable into a patient's rectum such that each of said plurality of fluid outlets is in fluid communication with the patient's colon, said rectal catheter having a first end, a second end and an outer wall extending between said first end and said second end, each of said plurality of fluid outlets extending through said outer wall, said plurality of fluid outlets being arranged in plurality of rows each extending from said first end toward said second end, each of said plurality of fluid outlets being elongated along an axis extending between said first end and said second end such that each of said plurality of fluid outlets has an ovoid shape; a balloon being positioned around said rectal catheter, said balloon being inflatable thereby facilitating said balloon to seal the patient's rectum wherein said balloon is configured to inhibit fluids from leaking outwardly from the patient's rectum, said balloon having a channel extending through a center of said balloon, said rectal catheter extending through said channel such that said balloon is positioned adjacent to said second end of said rectal catheter; a feed tube being fluidly coupled to said rectal catheter, said feed tube having a first injection port for insertably receiving an injection needle, said feed tube having a second injection port for insertably receiving an injection needle, said first injection port being in fluid communication with said balloon for inflating said balloon with the injection needle, said second injection port being in fluid communication with said rectal catheter for delivering a medication from the injection needle into said rectal catheter, said feed tube having a coupling port being in fluid communication with said rectal catheter, each of said first injection port and said second injection port angling away from an outer wall of said feed tube at a point being located adjacent to said coupling port, said feed tube having a first conduit being fluidly coupled between said first injection port and said balloon, said feed tube having a second conduit being fluidly coupled between said second injection port and said second end of said rectal catheter, each of said first injection port and said second injection port including a fluid lock being positionable between a closed condition or an open condition to control a flow of fluid through said fluid lock; an extension tube being fluidly coupled to said feed tube, said extension tube having a primary end being insertable into said coupling port on said feed tube; a tube lock being attached to said extension tube, said tube lock compressing said extension tube when said tube lock is closed thereby inhibiting a fluid from flowing through said extension tube, said tube lock being released from compressing said extension tube when said tube lock is open thereby facilitating the fluid to flow through said extension tube; a bag being fluidly attached to said extension tube such that said bag is in fluid communication with said rectal catheter thereby facilitating said bag to deliver and subsequently receive a fluid enema solution to said rectal catheter the fluid enema back through said rectal catheter, said bag having a fluid port being integrated into an outer wall of said bag, said fluid port insertably receiving a secondary end of said extension tube; and a hook being coupled to and extending upwardly from said bag thereby facilitating said bag to be suspended from a support to gravity feed the fluid enema solution to said rectal catheter, said hook having a distal end and a front edge extending between said bag and said distal end, said front edge being concavely arcuate between said bag and said distal end thereby facilitating said hook to conform to a rod of an intravenous bag support rack.

* * * * *